United States Patent [19]

Nicolaou et al.

[11] Patent Number: 5,237,101

[45] Date of Patent: Aug. 17, 1993

[54] PROPARGYLIC AND ALLENIC SULFONES

[75] Inventors: K. C. Nicolaou, La Jolla, Calif.; Guido Zaccarello, Philadelphia, Pa.; Golfo Skokotas; Peter Maligres, both of San Diego, Calif.

[73] Assignee: The Trustees of the Univ. of Penna., Philadelphia, Pa.

[21] Appl. No.: 470,814

[22] Filed: Jan. 26, 1990

[51] Int. Cl.$^5$ ............................................ C07C 315/00
[52] U.S. Cl. ...................................... 568/28; 568/32; 568/34
[58] Field of Search .............................. 568/28, 32, 34

[56] References Cited

PUBLICATIONS

Nicolaou, et al "A New Class of DNA-Cleaving Compounds" Angew. Chem. 101(9) pp. 1255-1257 (1989).
Yakovlev, et al "Disulfone Formation in the Reaction of Sodium Arenesulfinates with 4--Chloro-2-Butyn-1-ol" Zh. Obshch. Khim 57(1) pp. 237-238 (1987) Sec Chem. Abstr. vol. 107: 197678j, and p. 237.

Primary Examiner—John W. Rollins
Attorney, Agent, or Firm—Woodcock Washburn Kurtz Mackiewicz & Norris

[57] ABSTRACT

Propargylic and allenic sulfones are disclosed having the ability to selectively cleave nucleic acids, especially deoxyribonucleic acid. Such compositions are capable of being synthetically modified to effect cleavage at selected, sequenced sites on nucleic acids.

15 Claims, No Drawings

PROPARGYLIC AND ALLENIC SULFONES

GOVERNMENT SUPPORT

Portions of this invention were supported by National Institutes of Health Grant 2-ROI-GM-26879-09A1.

BACKGROUND OF THE INVENTION

This invention relates to the cleavage of nucleic acids, especially deoxyribonucleic acid (DNA) and, more specifically, to the cleavage of DNA by propargylic and allenic sulfones.

DNA is a very long, thread-like molecule which exists in the cells of most living organisms and which is intimately involved in the storage and transfer of genetic information. DNA is composed of discrete chemical units in sequences unique to the particular organism from which it is derived.

DNA cleavage is currently a topic of considerable research investigation, due in part to the recognition that certain molecules interact and bind with sites on a DNA molecule on the basis of the site's specific chemical sequence. Some of these DNA cleaving materials can cleave DNA at sequence specific sites. The sequence-specific cleavage of DNA is essential for many techniques in molecular biology, including gene isolation, DNA sequence determination, and recombinant DNA manipulation. Presently, such cleavage is performed largely with naturally-occurring restriction enzymes which bind and cleave DNA at particularly sequenced sites. However, because both the number and sequence specificities of such enzymes are limited, it is presently possible to cleave DNA only at a limited number of recognition sites.

It would be of great advantage to be able to cleave DNA at other predetermined sites; the design of sequence-specific DNA cleaving molecules that go beyond the specificities of natural enzymes could provide this capability. The ability to design molecules with predetermined specificities for selective cleavage would be of great importance for drug design, diagnostics, molecular biology, and materials chemistry.

The capability of selectively targeting a particularly sequenced site on a DNA and modifying it in some manner may thus provide a means of treatment for a disease or condition controlled by that site. For example, it has long been the desire of medicine to disrupt neoplasms such as cancer cells in animals, especially man. Such cells can likely be killed if their DNA were effectively, yet specifically, cleaved. While a number of molecules are known to facilitate DNA strand cleavage, many such compounds are believed to attack DNA in an organism's cells in a non-selective fashion. Because of the toxic nature of such nonselective DNA-reactive compounds, medicinal therapies which employ them have generally been reserved for advanced forms of cancer and other life-threatening diseases. With the advent of molecules which can selectively bind and cleave cancer cell DNA on the basis of a particular chemical sequence, new methods for the design of safe, effective, and highly specific, therapeutic agents, including anticancer agents could likely be developed. Interfering with DNA coding for other biological properties may provide therapeutic routes to non-neoplastic diseases as well. Accordingly, much effort has been directed toward the development of molecules that target and cleave chemically specific sites along a strand of DNA.

Both naturally-occurring and synthetic compounds have demonstrated the ability to cleave DNA under certain conditions; however, the presence of other reactive species has in many cases been a necessary predicate to effect the desired cleavage. For example, Zein, et al., Science, 240, 1198 (1988), have recently reported that a member of the calichemicin class of antibiotics cleaves DNA in a site-specific manner and that the ability to induce double-stranded DNA cleavage may account for the demonstrated antitumor activity of structurally related compounds. However, the mode of action for compounds belonging to these classes is thought to depend upon the attack of nucleophilic species. After recognition and interaction of a properly structured molecule from this class with DNA, the nucleophile is thought to trigger a sequence of intramolecular reactions centering on the unique bicyclic core structure. These reactions are believed to generate a highly reactive benzenoid diradical species through the cyclization of the conjugated enediyne moiety present within the bicyclic core. This species, in turn, is thought to react with and damage DNA's phosphate backbone.

While calichemicin and related compounds appear capable of cleaving DNA in nucleophilic environments, it would be of great advantage to be able to effect DNA cleavage under a wide variety of conditions, such as might be found within the human body, and with broad specificity.

It is therefore an object of this invention to provide chemical compounds which will cleave DNA.

It is another object of this invention to provide chemical compounds which will cleave DNA in a site-selective fashion.

It is yet another object of this invention to provide chemical compounds which will cleave DNA under a variety of conditions, especially under physiological conditions.

SUMMARY OF THE INVENTION

It has now been found that certain sulfone-containing chemical compounds possess the capacity to selectively cleave nucleic acids, especially DNA. Accordingly, this invention provides for the preparation and use of propargylic and allenic sulfones which cleave double-stranded DNA under a variety of conditions and which are capable of being synthetically modified to effect such cleavage at selected, sequenced sites.

The DNA-cleaving compounds of this invention are propargylic sulfones having general structures (1), (2), (3), and (4) together with allenic sulfones having general structures (5) and (6):

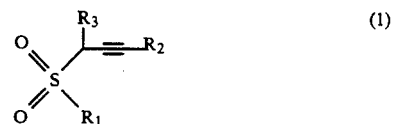

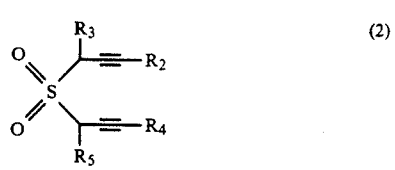

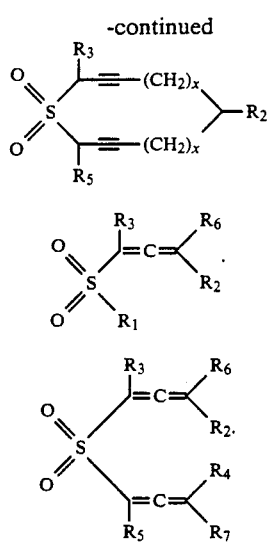

wherein $R_1$, $R_2$, $R_3$, $R_4$, $R_5$, $R_6$, and $R_7$ are, independently, hydrogen, hydroxyl, alkyl having from about 1 to about 10 carbon atoms, alkoxyl having from about 1 to about 10 carbon atoms, aryl having from about 6 to about 18 carbon atoms, $CH_2OC(O)CH_3$, $C(O)NHR_8$, $(CH_2)_nOH$, $(CH_2)_nO$-saccharides, $(CH_2)_n$-DNA intercalators, $(CH_2)_nO$-DNA minor groove binders, $(CH_2)_nO$-DNA binding proteins, $(CH_2)_nO$-DNA fragments, $(CH_2)_nO$ -ribonucleic acid (RNA) fragments, and $(CH_2)_nO$-antibodies; $R_8$ is a saccharide, DNA intercalator, DNA minor groove binder, DNA binding protein, DNA fragment, RNA fragment, or antibody; and $n = x = 1$–$10$, preferably 1–5. The bridgehead hydrogens of structure (4) can be cis or trans with respect to one another, although the cis configuration is preferred.

A wide variety of chemical functional groups may be appended to propargylic or allenic sulfones in accordance with this invention to engender site-selective cleavage of nucleic acids. Such functional groups are selected on the basis of their capacity to interact with one or more particularly sequenced sites on a RNA or DNA molecule. As will be understood by those skilled in the art, such molecular recognition and interaction are characterized in part by attractive forces having magnitude somewhat less than that of a covalent bond.

Alkyl moieties having from about 1 to about 30 carbon atoms provide one example of chemical functional groups which may be appended to the propargylic or allenic sulfones of this invention to enhance the interaction of such molecules with DNA or RNA. Such moieties are well-known to those of skill in the art and preferably have from about 1 to about 10 carbon atoms.

Aryl moieties also find similar use in the practice of this invention. As will be appreciated by those skilled in the art, such moieties typically possess aromatic carbocyclic structures. It is believed that the interaction of aryl moieties with nucleic acid sequences principally depends upon such aromaticity. Aryl moieties in accordance with this invention should have from about 6 to about 30 carbon atoms. Preferred are aryl moieties having from about 6 to about 15 carbon atoms; particularly preferred are phenyl, naphthyl, and anthryl moieties.

Saccharides also find use in the recognition and interaction of allenic and propargylic sulfones of this invention with nucleic acids. As will be appreciated by those of skill in the art, saccharides comprise carbon, hydrogen, and oxygen in such proportion that the ratio of hydrogen to oxygen is the same as that in water. Saccharides include tetroses, pentoses, and hexoses, and polymeric forms thereof. Examples of saccharides include sucrose, lactose, mal tose, fructose, glucose, galactose, and 6-deoxygalactose. Preferred among these are glucose, galactose, and 6-deoxygalactose.

Also useful as chemical functional groups appended to propargylic or allenic sulfones of this invention are compounds known to effect DNA mutation by intercalating in DNA. As will be appreciated by those skilled in the art, such DNA intercalators effect mutation by slipping between adjacent base pairs in the DNA double helix, leading to the insertion or deletion of one or more base pairs. DNA intercalators are commonly flat aromatic molecules such as the acridines. Indeed, preferred DNA intercalators in accordance with this invention include acridine, anthracene, ethidium bromide, quinacrine, and phenanthridine.

Certain chemical compounds are known by those skilled in the art to selectively interact with the DNA molecule at its minor groove. Such DNA minor groove binders find use as chemical functional groups which enhance the recognition and interaction of allenic and propargylic sulfones of this invention with nucleic acids. Exemplary DNA minor groove binders include distamycin and netropsin.

In addition, certain proteins and antibodies are known to interact with or even bind DNA in site-selective fashion. Such proteins and antibodies find use in enhancing the recognition and interaction DNA with the chemical compounds of this invention. Examples of DNA binding proteins are tryptophan gene repressor, Hin recombinase, and Hin 52mer binding fragment. Suitable antibodies include monoclonal or polyclonal antibodies specific for nucleic acid (RNA or DNA) or adjunct components of DNA or RNA. A preferred example of such antibodies is mAb 9.2.27 (Ig G2a).

Many different types of chemical functional groups can be appended to the propargylic or allenic sulfone moieties of this invention to engender site-selective cleavage of DNA. For example, propargylic or allenic sulfones may be modified for a particular site-specific cleavage by first synthesizing a relatively simple molecule, such as the alcohol of structure (7), and then attaching to it by generally known chemical procedures one or more chemical functional groups having an affinity for a targeted site on the DNA molecule. Such functionality can be chosen as appropriate for any number of DNA cleaving applications. For example, in order to selectively cleave the DNA unique to cancerous mammalian liver cells one would first identify one or more chemical functional groups exhibiting physicochemical affinity for that DNA. Once identified, such functional groups are covalently bound by appropriate means to one or more propargylic and allenic sulfones according to this invention. Molecules thus synthesized are then put in contact with the targeted DNA. Such contact may be effected by topical application, ingestion, or injection of formulations comprising the chemical compounds of this invention. As will be appreciated by those skilled in drug delivery and related arts, there exists numerous means by which a given type of DNA might be contacted with the propargylic and allenic sulfones of this invention. It is intended that the present invention encompass all such contacting means.

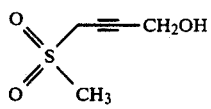 (7)

While many different types of chemical functional groups can be appended to the DNA-cleaving propargylic and allenic sulfones of this invention, preferred compounds include: structure (1) where $R_1$ is phenyl, $R_2$ is $CH_2OH$, and $R_3$ is hydrogen; structure (1) where $R_1$ is anthryl, $R_2$ is $CH_2OH$, and $R_3$, is hydrogen; structure (1) where $R_1$ is naphthyl, $R_2$ is $CH_2OH$, and $R_3$, is hydrogen; structure (2) where $R_2$ and $R_4$ are $CH_2OH$, and $R_3$, and $R_5$ are hydrogen; structure (3) where $R_2$ is hydroxyl, $R_3$ and $R_5$ are hydrogen, and $x=1$; structure (4) where $R_2$ and $R_4$ are $CH_2OH$, $R_3$ and $R_5$ are hydrogen and $x=1$; structure (4) where $R_2$ and $R_4$ are $CH_2OH$, $R_3$ and $R_5$ are hydrogen, and $x=2$; structure (4) where $R_2$ and $R_4$ are $CH_2OH$, $R_3$ and $R_5$ are hydrogen, and $x=3$; structure (4) where $R_2$ and $R_4$ are $CH_2OH$, $R_3$ and $R_5$ are hydrogen, and $x=4$; structure (5) where $R_1$ is phenyl, $R_2$ is $CH_2OH$, and $R_3$ and $R_6$ are hydrogen; structure (5) where $R_1$ is phenyl, $R_2$ and $R_6$ are hydrogen, and $R_3$, is $CH_2OH$; and structure (5) where $R_1$ is naphthyl, $R_2$ is $CH_2OH$, and $R_3$ and $R_6$ are hydrogen.

Especially preferred DNA-cleaving compounds include: structure (1) where $R_1$ is anthryl, $R_2$ is $CH_2OH$, and $R_3$ is hydrogen; structure (1) where $R_1$ is naphthyl, $R_2$ is $CH_2OH$, and $R_3$, is hydrogen; structure (2) where $R_2$ and $R_4$ are $CH_2OH$, and $R_3$ and $R_5$ are hydrogen; structure (4) where $R_2$ and $R_4$ are $CH_2OH$, $R_3$ and $R_5$ are hydrogen and $x=1$; and structure (5) where $R_1$ is naphthyl, $R_2$ is $CH_2OH$, and $R_3$ and $R_6$ are hydrogen.

It is preferred that the methods of this invention be practiced at pH above about 7; it is especially preferred that they be practiced at pH between about 7 and about 10.

The compounds of the invention may preferably be linked, especially covalently linked, with sequences of nucleic acid, DNA or RNA, for site-specific cleavage of target DNA or RNA. The base sequence of the attached nucleic acid is selected to be complementary to the site where cleavage is desired such that hybridization occurs. The nucleic acid sequence can be readily prepared by chemical synthesis, for example, using a DNA synthesizer and commercially available reagents and subsequently linked with a compound of the invention for cleavage of DNA. Nucleic acid sequences should have from about three to about twenty nucleotide bases. It is preferred that nucleic acid sequences have from about five to about ten nucleotide bases. By the use of the compounds of the invention linked with nucleic acid sequences, cleavage of nucleic acids can be achieved at pre-selected sites, without dependence on the use of restriction enzymes.

The ability to select a cleavage site having any nucleotide base sequence is particularly useful in assays for the detection of a specific mutation or change in base sequence. A nucleic acid sequence having a base sequence complementary to the mutated region and attached to a compound of the invention can be used to target the mutation in a test sample of nucleic acid. If the mutation or change is present in the test nucleic acid, the complementary sequence will bind and the nucleic acid will be cleaved; if not, cleavage of the test nucleic acid will generally not occur.

The products of DNA cleavage presently have great utility in biomedical research. For example, DNA cleavage currently provides a means for isolating new combinations of genes in the laboratory. These novel genes can then be inserted into suitable host cells in accordance with known methods and cloned by the DNA synthesizing system of the host. The employment of DNA cleavage products in this manner can result in the syntheses of large quantities of otherwise scarce proteins by such clones. DNA cleavage is also a vital step in processes such as those embodied by U.S. Pat. No. 4,736,866, Leder et al., for the creation of genetically altered animals. This process employs enzymatic techniques to cleave DNA. As mentioned, enzymatic techniques have limitations which might well be overcome by the development of site-specific synthetic molecules which could be coupled with the compounds of this invention to enable DNA cleavage at a wider variety of sites than is presently available.

The results of the following examples confirm that the relatively simple sulfone-containing allenic and propargylic compounds of this invention cleave DNA. Incorporation of core structures (1), (2), (3), (4), (5), or (6) or of related structures into molecular assemblies bearing suitable site-specific moieties will likely result in powerful biotechnological reagents; they may also be useful therapeutic and diagnostic agents for the treatment of cancer and other disease.

The invention is now further described in connection with the following examples thereof wherein parts and percents are by weight unless otherwise specified. The article Nicolaou, et al., "A New Class of DNA-Cleaving Molecules: pH-Dependent DNA Cleavage by Propargylic and Allenic Sulfones", Angew. Chem. Int. Ed. Engl. 28 1989, 9, 1272, is incorporated herein by reference.

EXAMPLE 1

Epichlorohydrin was reacted with 2.2 equivalents of tetrahydro-2-(2-propynloxy)-2H-pyran (THPO-$CH_2C\equiv CH$), 2.0 equivalents of n-butyllithium (n-BuLi), and 2.0 equivalents of boron trifluoride etherate in tetrahydrofuran (THF) at $-78°$ C. The mixture was stirred and over the course of 12 hours the temperature was raised to 25° C. The acyclic product was isolated in 94% yield and reacted with 1.1 equivalents of sodium methoxide in methanol at 25° C. over 12 hours. The cyclized product was isolated in 74% yield and reacted with 2.0 equivalents of THPO-$CH_2C\equiv CH$, 2.2 equivalents of n-BuLi, and 2.2 equivalent of boron trifluoride etherate in THF at $-78°$ C. The reaction mixture was stirred and over the course of 2 hours and the temperature was allowed to rise to 25° C. The chemical compound having structure (8) ($R_9$=OTHP, $R_{10}$=H) was isolated in 58% yield. This product was then reacted with 1.2 equivalents of t-butyldiphenylsilyl chloride ($^t$BuPhSiCl) and 2.0 equivalents of imidazole in dimethylformamide (DMF). The reaction was stirred at 25° C. over 12 hours and a compound having structure (8) ($R_9$=THP, $R_{10}$=Si$^t$BuPh$_2$) was isolated in 44% yield. This compound was then reacted with 0.2 equivalents of pyridinium p-toluene sulfonate (PPTS) in methanol. The reaction was stirred at 25° C. over 12 hours and the chemical compound having structure (8) ($R_9$=OH, $R_{10}$=Si$^t$BuPh$_2$) was isolated in 92% yield. This compound was then reacted with 2.2 equivalents o f carbon tetrabromide (CBr$_4$) and 2.7 equivalents of trioctylphosphine (P(oct)$_3$) in diethyl ether at 0° C. The reaction was allowed to stir for a 4 hour interval, during which the temperature rose to 25° C. The chemical compound having the structure (9) (R$_9$=Br, R$_{10}$=Si$^t$BuPh$_2$) was isolated in 84% yield. It was then reacted with 2.0 equivalents of Na$_2$S.Al$_2$O$_3$ in a solution of methylene chloride and ethanol (5:2). The reaction was stirred at 25° C. for 2 hours and the chemical compound having structure (9) (R$_{10}$=Si$^t$BuPh$_2$) was isolated in 55% yield. This compound was then reacted with 4.0 equivalents of m-chloroperoxybenzoic acid (mCPBA) in methylene chloride at 0° C. The reaction was allowed to stir for 3 hours at 25° C. and a product having structure (3) (R$_2$=OSi$^t$BuPh$_2$, R$^3$=R$^5$=H and x=1) was isolated in 87% yield. This compound was then treated with a 48% aqueous solution of hydrofluoric acid and acetonitrile (1:5). The mixture was allowed to stir at 25° C. over 16 hours and the chemical compound having structure (3) (R$_2$=OH, R$_3$=R$_5$=H and x=1) was isolated in 30% yield.

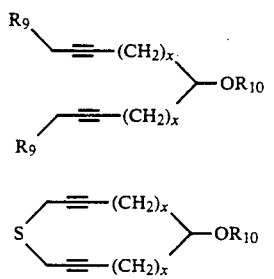

EXAMPLE 2

9 Anthracenethiol was reacted with 1.1 equivalents of sodium hydride and 0.75 quivalents of the chemical compound BrCH$_2$C≡CCH$_2$-OSi$^t$BuPh$_2$ in DMF at 0° C. The reaction was stirred for 5 hours, during which the temperature was allowed to rise to 25° C. The adduct was isolated in 100% yield. This compound was then reacted with 3.0 equivalents of mCPBA in methylene chloride at 0° C. The reaction was allowed to stir for 4 hours, during which the temperature was allowed to rise to 25° C. The chemical compound having structure (1) (R$_1$=anthryl, R$_2$=CH$_3$OSi$^t$BuMe$_2$, R$_3$=H) was isolated in 75% yield, and then treated with a 48% aqueous solution of hydrofluoric acid and acetonitrile (1:5) at 0° C. The temperature was allowed to rise to 25° C. with stirring over the course of 15 minutes. The chemical compound having structure (1) (R$_1$=anthryl, R$_2$=CH$_3$OH, and R$_3$=H) was isolated in 90% yield.

EXAMPLE 3

A compound having structure (10) (R$_2$=R$_4$=CH$_2$OSi$^t$BuPh$_2$, x=1) was synthesized has set forth in J. Am. Chem. Soc. 1988 110, 7247. This compound was treated with four equivalents of mCPBA in methylene chloride at 0° C. Over the course of two hours the reaction was allowed to rise to 25° C. and a compound having structure (4) (R$_2$=R$_4$ OSi$^t$-BuPH$_2$, cis bridgehead hydrogens) was isolated in 80% yield. This compound was next reacted with 48% aqueous HF:CH$_3$CN (14) at 0° C. Over the course of two hours the reaction was allowed to rise to 25° C. and a product having structure (4) (R$_2$=R$_4$=CH$_2$OH, x=1, cis bridgehead hydrogens) was isolated in 98% yield.

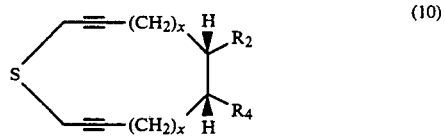

EXAMPLE 4

A compound having structure (11) (R$_2$=R$_4$=CH$_2$OSi$^t$BuPh$_2$) was synthesized by the technique set forth in J. Am. Chem. Soc. 1988, 110, 7247. This compound was treated with ozone in ethyl acetate (EtOAc):CH$_3$OH (4:1) at −78° C. for 0.25 hours and then 1.0 equivalent of sodium borohydride (NaBH4). Over the course of one hour the reaction was allowed to rise to 25° C., the product was isolated in 76% yield, and was treated with 2.2 equivalents of CBr$_4$ and 2.75 equivalents of P(oct)$_3$ in diethyl ether (Et$_2$O) at 0° C. Over the course of one hour, the reaction was allowed to rise to 25° C. and the product having structure (12) (R$_{10}$=Br, x=2) was isolated in 45% yield. This product was then treated with 2.2 equivalents of THPO-CH$_2$C≡CH and 2.2 equivalents of n-BuLi in hexamethylphosphoramide (HMPA):THF (1:13) at −78° for two hours. The product was isolated in a 45% yield and treated with 0.25 equivalents of toluene sulfonic acid (TsOH) in CH$_3$OH:Etz$_2$O (5:1) at 25° C. for one hour. The product was isolated in 84% yield and was treated with 2 2 equivalents of CBr$_4$ and 2.75 equivalents of P(oct)$_3$ in Et$_2$O at 0° C. Other the course of six hours, the reaction was allowed to rise to 25° C. and the product having structure (12) (R$_{10}$=C≡CCH$_2$Br, x=2) was isolated in 40% yield. This product was treated with 2.0 equivalents of Na$_2$S.Al$_2$O$_3$ in CH$_2$Cl$_2$:EtOH 5:2) at 25° C. for two hours. The product was isolated in 75% yield, and treated with 4.0 equivalents with mCPBA in methylene chloride at 0° C. Over the course of two hours the reaction was allowed to rise to 25° C. and the product, isolated in 85% yield, was treated with 48% aqueous HF:CH$_3$CN (1:4) at 0° C. Over the course of two hours, the reaction was allowed to rise to 25° C. and a product having structure (4) (R$_2$=R$_4$=CH$_2$OH, R$_3$=R$_5$=H, x=2, cis bridgehead hydrogens) was isolated in 85% yield.

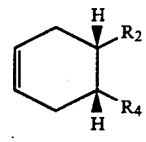

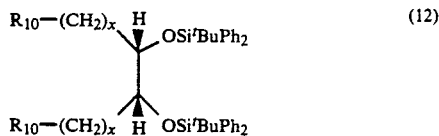

EXAMPLE 5

A compound having structure (12) (R$_{10}$=CO, x=1) was synthesized by the techniques set forth in J. Am. Chem. Soc. 19889, 110, 7247. This compound was treated with 2.25 equivalents of (CH$_3$O)$_2$P(O)CH$_2$C(O)OCH$_3$ and 2.25 equivalents of NaH in THF at 0° C. Over the course of four hours, the reaction was allowed to rise to 25° C. and the product, isolated in 75% yield, was treated with 20% Pd(OH)2/C (moist) and H2 in EtOAc at 25° C. for 16 hours. A product was isolated in 97% yield and treated with 4.4 equivalent of diisobutyl aluminum hydride (DIBAL) in toluene at −78° C. Over the course of one hour, the reaction was allowed to rise to 0° C. and a product having structure (12) ($R_{10}$=CH2OH, x=3) was isolated in 77% yield. This product was treated with 4.0 equivalents of pyridinium chlorochromate (PCC) and 4 angstrom molecular sieves in methylene chloride at 0° C. Over the course of two hours, the reaction was allowed to rise to 25° C. and the product, isolated in 64% yield, was treated with 4.0 equivalents of CBr4 and 8.0 equivalent of triphenylphosphine (PPh3) in methylene chloride at 0° C. for one hour. The product, which was isolated in 54% yield, was then treated with 4.5 equivalents of n-BuLi in THF at −78° C. for 0.5 hours. This reaction was then treated with 10.5 equivalents of ClC(O)OCH3 at −78° C. Over the course of one hour, the reaction was allowed to rise to 25° C. and a product having structure (12) ($R_{10}$=C≡CC(O)OCH3, x=3) was isolated in 60% yield. This product was then treated with 6.8 equivalents of DIBAL in toluene at −78° C. for two hours. The product, isolated in 85% yield, was then treated with 2.2 equivalents of CBr4 and 2.75 equivalents of P(oct)3 in Et2O at 0° C. Over the course of three hours, the reaction was allowed to rise to 25° C. and a product was isolated in 85% yield. This product was then treated with 2.0 equivalents of Na2S.Al2O3 in CH2Cl2:EtOH (5:2) at 25° C. for one hour. A product having structure (10) ($R_2$=$R_4$=CH2OSi$^t$BuPh2, x=3) was isolated in 57% yield and treated with 4.0 equivalents of mCPBA in methylene chloride at 0° C. over the course of one hour, the reaction was allowed to rise to 25° C. and a product isolated in 71% yield. This product was then treated with 48% aqueous HF:CH3CN (1:4) at 0° C. Over the course of 12 hours, the reaction was allowed to rise to 25° C. and a product having structure (4) ($R_3$=$R_5$=H, $R_2$=$R_4$=CH2OH, x=3, cis bridgehead hydrogens) was isolated in 95% yield.

EXAMPLE 6

The compound having structure (12) ($R_{10}$OH, x=4) was treated with 2.2 equivalents of CBR4 and 3.0 equivalents of P(oct)3 in THF at 25° C. for 48 hours. A product was isolated 97% yield, and was treated with 3.9 equivalents of THPO-CH2C≡CH and 3.5 equivalents of n-BuLi in 1,3-dimethyl-3,4,5,6-tetrahydro-2(1H)-pyrimidione (DMPU):THF (1:2) at −78° C. Over the course of 16 hours, the reaction was allowed to rise to 25° C. and a product isolated in 75% yield. This product was then treated with 0.2 equivalents of PPTS in CH3OH at 64° C. for one hour, yielding a product having structure (12) ($R_{10}$=C≡CCH2OH, x=4) in 93% yield. This product was treated with 2.5 equivalents of CBr4 and 4.7 equivalents of tributylphosphine (PBu3) in THF at 0° C. for 0.2 hours. This product (91% yield) which was then treated wtih 2.0 equivalents of Na2S.Al2O3 in CH2Cl2:EtOH (5:2) at 25° C. for three hours. A compound having structure (10) ($R_2$=$R_4$=CH2OSi$^t$BuPh2, x=4) was isolated and was treated with K2HPO4 and 3.0 equivalents of mCPBA in methylene chloride at 0° C. The product was isolated and treated with 48% aqueous HF:CH3CN (1:5) at 25° C. for two hours, yielding a product having structure 4 ($R_3$=$R_5$=H, $R_2$=$R_4$=CH2OH, x=4, cis bridgehead hydrogens) in 90% yield.

EXAMPLE 7

A compound having structure (13) was synthesized as set forth in J. Am. Chem. Soc., 1980, 102, 2005. This compound was treated with 2.1 equivalents of $^t$BuPh2SiCl and 2.1 equivalents of imidazole with a catalytic amount of dimethylaminopyridine (DMAP) in dimethylformamide (DMF) at 0° C. Over the course of six hours, the reaction was allowed to rise to 25° C. and a quantitative yield of product obtained. This product was treated with ozone in CH2Cl2:CH3OH (7:1) at −78° C. The reaction was the treated with 2.0 equivalents of triethyl phosphite (P(OEt)3) at −78° C. Over the course of the next 2.5 hours, the reaction was allowed to rise to 25° C. and a product having structure (14) ($R_{10}$=CO, x=1) was isolated. This compound was treated with 3.2 equivalents of CBr4 and 6.0 equivalents of PPh3 in methylene chloride at 0° C. for 1.5 hours. The product of the last two steps was isolated in 85% yield and treated with 5.9; equivalents of n-BuLi in THF at −78° C. for one hour and then 10.0 equivalents of Clc(O)OCH3. Over the next 16 hours the reaction was allowed to rise to 25° C. and a product isolated in 77% yield. This product was then treated with 4.6 equivalents of DIBAL in methylene chloride at 0° C. for 0.5 hours. A product having structure (14) ($R_{10}$=C≡CCH2OH, x=1) was isolated in 98% yield, and then treated with 2.2 equivalents of CBr4 and 4.4 equivalents of PBu3 in THF at 0° C. for 0.5 hours. The product was isolated in 80° yield and treated with 2.0 equivalents of Na2S.Al2O3 in CH2Cl2:EtOH (5:2) at 25° C. for 2.5 hours. A product having structure (15) ($R_2$=$R_4$=CH2OSi$^t$BuPh2, x=1) was isolated in 93% yield and treated with K2HPO4 and 3.6 equivalents of mCPBA in methylene chloride at 25° C. for 1.0 hours, giving a product in 88% yield. This product was then treated with 48% aqueous HF:CH3CN (1:5) at 25° C. for 3.5 hours, giving a product having structure (4) ($R_3$=$R_5$=H, $R_2$=$R_4$=CH2OH, x=1, trans bridgehead hydrogens) in 76% yield.

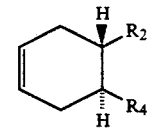

(13)

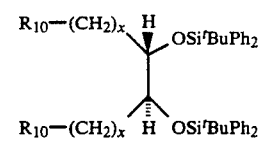

(14)

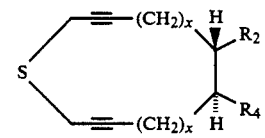

(15)

EXAMPLE 8

THPO-CH2C≡CH was treated with 1.1 equivalents of n-BuLi in THF at −78° C. for 0.5 hours and then 1.4 equivalents of paraformaldehyde ((CH2O)$_n$) Over the course of 12 hours, the reaction was allowed to rise to 25° C. and a product isolated in 84% yield. This product was then treated with 1.6 equivalents of P(oct)3 in CCl4 at 25° C. for six hours, yielding THPO-CH$_2$C≡CCH$_2$Cl in 85% yield. This compound was then treated with 1.0 equivalents NA$_2$S.9H$_2$O in EtOH:H$_2$O (10:1) at 25° C. for 12 hours. The product, which was isolated in 47% yield, was then treated with acetic acid (AcOH):H$_2$O:THF (7:3:10) at 25° C. for 12 hours. The resulting product, which was isolated in 64% yield, was then treated with 3.0 equivalents of mCPBA in methylene chloride for 2 hours yielding a compound having structure (2) (R$_3$=R$_5$=H, R$_2$=R$_4$=CH$_2$OH) in 40% yield.

EXAMPLE 9

The compound THPO-CH$_2$C≡CCH$_2$Cl was treated with 2.0 equivalents of thiophenol (PhSH) and 1.5 equivalents of NaH in DMF at 0° C. Over the course of one hour, the temperature was allowed to rise to 25° C. The product, isolated in 83% yield, was treated with acetic acid (AcOH):H$_2$O:THF (7:3:10) at 25° C. for 24 hours. The product, isolated in 30% yield, was then treated with 3.0 equivalents of mCPBA in methylene chloride at 0° C. Over the course of 2 hours, the reaction was allowed to rise to 25° C. and a product having structure (1) (R$_1$=phenyl, R$_2$=CH$_2$OH, R$_3$=H) was isolated in 75% yield.

EXAMPLE 10

A compound having structure (16) was synthesized as set forth in *J. Chem. Soc. Perkin Trans I* 1975, 687. This compound was treated with sulfuric acid in methanol at 40° C. for two hours, yielding structure (17) in 32% yield. This compound was then treated with 1.0 equivalents of $^t$BuPh$_2$SiCl and 1.5 equivalents of imidazole in DMF at 25° C. for one hour. A product, isolated in 43% yield, was then treated with 1.0 equivalents of PhSCl and 1.1 equivalents of triethylamine (Et$_3$N) in methylene chloride at 25° C. for 3 hours. A product having structure (18) (R$_{10}$=CH$_2$-OSi$^t$BuPh$_2$, R$_3$=H) was isolate in 75% yield and treated with 1.5 equivalents of mCPBA in methylene chloride at 25° C. for one hour. A product was isolated in 84% yield and treated with 48% aqueous HF:CH$_3$CN (1:5) at 25° C. for two hours, yielding a compound having structure (5) (R$_1$=phenyl, R$_3$=H, R$_2$=H, R$_6$=CH$_2$OH) in 96% yield.

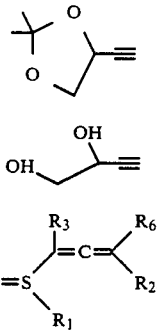

(16)

(17)

(18)

EXAMPLE 11

The compound $^t$Bu(CH$_3$($_2$SiOCH$_2$C≡C was synthesized as set forth in *J. Antibiotics* 1984, 37, 733. This compound was treated with 1.1 equivalents of n-BuLi in THF at −78° C. for 0.5 hours and then 1.2 equivalents of (CH$_2$O)$_n$. Over the course of 12 hours, the reaction was allowed to rise 25° C. A product, isolated in 74% yield, was treated with 1.0 equivalents of PhSCl and 1.0 equivalents of Et$_3$N in methylene chloride at 0° C. Over the course of 12 hours, the reaction was allowed to rise to 25° C., and a product having structure (22) (R$_3$=CH$_2$OSi$^t$BuMe$_2$, R$_{10}$=H) was isolated in 68% yield. This compound was treated with 1.0 equivalents of diphenyl diselenide (PhSeSePh) and 30% aqueous H$_2$O$_2$(1M) in THF at 25° C. for seven hours. A product, isolated in 21% yield, was then treated with 48% aqueous HF:CH$_3$CN (1:5), at 0° C. for one hour. A compound having structure (5) (R$_1$=phenyl, R$_2$=R$_6$=H, R$_3$=CH$_2$OH) was isolated in 72% yield.

EXAMPLE 12

Cleavage of DNA

To a vial containing a 50 micromolar per base pair solution of uX74 Type I double-stranded DNA in 2.0 micro liters pH 8.5 tris-HCl buffer was added 6.0 microliters of a pH 8.5 trisHCl buffer solution and 2.0 microliters of a 5.0 micromolar aqueous solution of the chemical compound prepared in Example 1. The same procedure was repeated for the compound produced in Example 2.

The vials were then placed in a 37° C. oven for 24 hours. A 2.0 microliter portion of glycerol loading buffer solution containing bromothymol blue indicator was added to each vial. A 10 mi crol iter aliquot was the n drawn from each. Gel electrophoresis analysis of the aliquots was then performed using a 1.0% agarose gel with ethidium bromide run at 115 volts for 1 hour. DNA cleavage was indicated by the formation of Type II DNA, which was detected by visual inspection of the gel under 310 nanometer ultraviolet light.

What is claimed is:

1. A chemical compound having the structure:

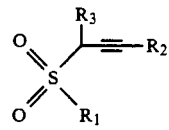

wherein R$_1$, R$_2$, and R$_3$ are independently hydrogen, hydroxyl, alkyl moieties having from about 1 to about 10 carbon atoms, and aryl moieties having 11 to about 18 carbon atoms, CH$_2$OC(O)Ch$_3$, C(O)NHR$_8$, (CH$_{2n}$OH, (CH$_{2n}$O-saccharides, (CH$_2$)$_n$O-DNA intercalators, (CH$_2$)$_n$O-DNA minor groove binders, (CH$_2$)$_n$)O-DNA binding proteins, (CH$_2$)$_n$O-DNA fragments, (CH$_2$)$_n$)O-RNA fragments, or (CH$_2$)$_n$O-antibodies, R$_8$ is selected from the group consisting of saccharides, DNA intercalators, DNA minor groove binders, DNA binding proteins, DNA fragments, RNA fragments, or antibodies and n=1-10.

2. The chemical compound of claim 1 wherein R$_1$ is anthryl, R$_2$ is CH$_2$OH and R$_3$ is hydrogen.

3. The compound of claim 1 wherein R$_1$, R$_2$, or R$_3$ is hydrogen.

4. The compound of claim 1 wherein R$_1$, R$_2$, or R$_3$ is hydroxyl.

5. The compound of claim 1 wherein R$_1$, R$_2$, or R$_3$ is an alkyl moiety having from 1 to about 10 carbon atoms.

6. The compound of claim 1 wherein R$_1$, R$_2$, or R$_3$ is an aryl moiety having 11 to about 18 carbon atoms.

7. The compound of calim 1 wherein R$_1$, R$_2$, or R$_3$ is CH$_2$OC(O)CH$_3$.

8. The compound of claim 1 wherein R$_1$, R$_2$or R$_3$ is C(O)NHR$_8$.

9. The compound of claim 1 wherein $R_1$, $R_2$, or $R_3$ is $(CH_2)_nOH$.

10. The compound of claim 1 wherein $R_1$, $R_2$, or $R_3$ is $(CH_2)_nO$-saccharide.

11. The compound of claim 1 wherein $R_1$, $R_2$, or $R_3$ is $(CH_2)_nO$-DNA intercalator.

12. The compound of claim 1 wherein $R_1$, $R_2$, or $R_3$ is $(CH_2)_nO$-DNA minor groove binder.

13. The compound of claim 1 wherein $R_1$, $R_2$, or $R_3$ is $(CH_2)_nO$-DNA binding protein.

14. The compound of claim 1 wherein $R_1$, $R_2$, or $R_3$ is $(CH_2)_nO$-DNA fragment or $(CH_2)_nO$-RNA fragment.

15. The compound of claim 1 wherein $R_1$, $R_2$, or $R_3$ is $(CH_2)_nO$-antibody.

* * * * *